United States Patent [19]

Nagpal

[11] 4,443,474
[45] Apr. 17, 1984

[54] PHARMACEUTICAL N-PHENYL CARBAMOYL GLYCINATE COMPOSITIONS

[75] Inventor: Krishen L. Nagpal, Williamsville, N.Y.

[73] Assignee: Buffalo Color Corporation, West Paterson, N.J.

[21] Appl. No.: 406,009

[22] Filed: Aug. 6, 1982

[51] Int. Cl.³ .................. C07C 101/24; A61K 31/24
[52] U.S. Cl. ....................................... 424/309; 560/34
[58] Field of Search .................. 560/34, 43; 424/309

[56] References Cited

PUBLICATIONS

Aspelund, Chem. Abst., vol. 59, (1963), 2798–2799.
Chemical Abst., Decennial Index, vols. 1–10, (1907–1916), Subject Index CR–K 3187.

*Primary Examiner*—Bernard Helfin
*Attorney, Agent, or Firm*—Michael L. Dunn; William J. Crossetta

[57] ABSTRACT

N-phenyl carbamoyl glycinate compounds of the formula

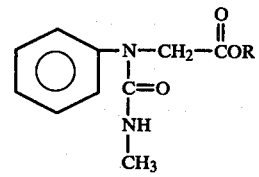

wherein R is lower alkyl, are disclosed as having anti-convulsant activity; and, methods are disclosed for producing anti-convulsant activity by administering pharmaceutical compositions containing at least one of said compounds.

13 Claims, No Drawings

PHARMACEUTICAL N-PHENYL CARBAMOYL GLYCINATE COMPOSITIONS

TECHNICAL FIELD

The control of undesired convulsant activity in animal organisms by the application of pharmaceutical compositions is a continuing need. For human patients with epilepsy, the development of new anti-epileptic drugs may offer the only hope for achieving control of their seizures.

Though a multiple of anti-epileptic drugs are available, there is still a continuing need for new anti-epileptic drugs with more selective anti-convulsant effects and less toxicity. A detailed description of the history and development of various drugs marketed for their anti-epileptic activity can be found in the publication Epilepsia, Vol. 19, pages 393–428, 1978, Raven Press, New York.

DESCRIPTION OF THE INVENTION

This invention relates to novel N-phenyl carbamoyl glycinate pharmaceutical compositions having anti-convulsant activity and to methods of producing anti-convulsant activity by administering said compositions. More specifically the compositions of this invention contain an anti-convulsant amount of at least one compound of the formula:

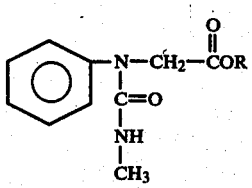

wherein R is lower alkyl; as the active ingredient.

The novel pharmaceutical compositions of this invention, in dosage unit form, comprise a non-toxic pharmaceutical carrier and an effective anti-convulsant activity inducing amount of lower alkyl-N-phenyl-N-methylcarbamoyl glycinate.

Representative lower alkyl groups encompassed within the description of R include branched and straight chain methyl, ethyl, propyl, butyl, pentyl and hexyl. Preferred lower alkyl contain from 1 to 4 carbon atoms and especially preferred are methyl, ethyl, n-butyl and isobutyl.

The compounds of this invention can typically be prepared by reacting a lower alkyl-N-phenyl glycinate with a methyl isocyanate in the presence of a suitable solvent in accord with the following ammonolysis

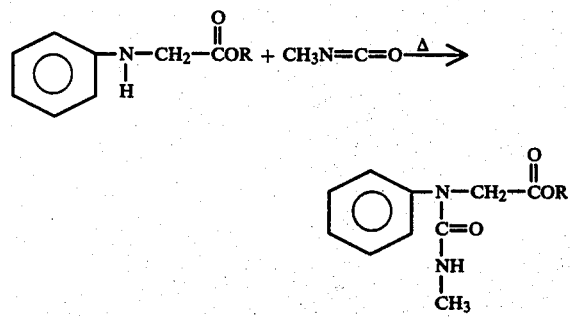

To maintain a reasonable rate of reaction, typical conditions require a reaction temperature from about 30° C. to about 200° C. and a reaction time of from about several minutes to two days or more. The reaction can proceed without a solvent but typically a suitable unreactive solvent is utilized such as toluene and the like.

After the reaction has been completed the volatiles are removed from the reaction product mixture and the desired product can be readily attained from the residue by standard extraction techniques.

Typical compounds falling within the invention include; methyl-N-phenyl-N-methylcarbamoyl glycinate; ethyl-N-phenyl-N-methylcarbamoyl glycinate; n-propyl-N-phenyl-N-methylcarbamoyl glycinate; i-propyl-N-phenyl-N-methylcarbamoyl glycinate; n-butyl-N-phenyl-N-methylcarbamoyl glycinate; i-butyl-N-phenyl-N-methylcarbamoyl glycinate; t-butyl-N-phenyl-N-methylcarbamoyl glycinate; s-butyl-N-phenyl-N-methylcarbamoyl glycinate; n-pentyl-N-phenyl-N-methylcarbamoyl glycinate; i-pentyl-N-phenyl-N-methylcarbamoyl glycinate; N-hexyl-N-phenyl-N-methylcarbamoyl glycinate and the like.

The anti-convulsant activity of the compositions of the invention is measured by the ability of the active medicament, the lower alkyl-N-phenyl-N-methylcarbamoyl glycinate, to control adjuvant induced convulsions in laboratory test animals.

The testing for anti-convulsant activity of the compounds of this invention was performed by the National Institute of Neurological and Communicative Disorders and Stroke (NINCDS) using a comprehensive biological testing program established to aid the development of new anti-epileptic agents for use in primates. As part of the program, compounds are evaluated for central nervous system toxicity by a rotorod ataxia test and for anti-convulsant activity in two seizure models, the Maximal Electroshock Seizure test and the Subcutaneous Pentylenetetrazol Seizure Threshold test. The two models of seizure provocation have been characterized as reliably eliciting seizure phenomena and together with the ataxia test are considered by NINCDS as sufficient to identify anti-convulsant activity. Activity displayed against electroshock induced seizure is considered to indicate activity against "grand mal" seizure; while activity against sub-cutaneous chemical induced seizure is considered to indicate activity against "petit mal" seizures.

In the Maximal Electroshock Seizure test, maximum seizure is induced in laboratory mice by corneal stimulation with 60 Hz of 50 mA alternating current. The maximum seizure lasts about 22 seconds and typically consists of a short period of initial tonic flexion and a prolonged period of hind limb tonic extension. Abolition of the hind limb tonic extensor component is considered as indicating anti-convulsant activity in the test compound.

In the Sub-cutaneous Pentylenetrazol Seizure test, threshold seizure is induced by sub-cutaneous administration of pentylenetetrazol in laboratory mice. Failure to observe a threshold seizure (at least one spasm of 5 sec. duration) is considered as indicating anti-convulsant activity in the test compound.

In the rotorod ataxia test, laboratory mice are placed on a one inch diameter rotating (6 RPM) rod. Normal mice can remain thereon indefinitely while a neurological deficit is defined as the failure of the animal to remain on the rod at least one minute.

The anti-convulsant testing was carried out at dosages of 30, 100 and 300 mg/kg of body weight and at 30 minutes and 4 hours after medicament administration. Twelve animals were used, four at each dosage level.

The pharmaceutical compositions of the invention can be prepared in conventional dosage unit forms by incorporating an amount of lower alkyl-N-phenyl-N-methylcarbamoyl glycinate to produce anti-convulsant activity, without toxic effect, with a non-toxic pharmaceutical carrier, according to accepted procedures.

The pharmaceutical carrier or diluent employed may be a solid or liquid in any suitable physical form. Examples of solid carriers include lactose, terra alba, sucrose, talc, gelatin, agar, pectin, acacia, magnesium, stearate, stearic acid and the like. Typical liquid carriers include syrup, peanut oil, olive oil, water and the like. Similarly, the carrier or diluent can include time delay materials such as glyceryl monostearate or glyceryl distearate alone or in wax and the like. The pharmaceutically active composition may also contain other active compounds, adjuvants, stabilizers, conditioners, fillers and the like providing they do not unduly interfere with the activity of the lower alkyl-N-phenyl-N-methylcarbamoyl glycinate ingredient or do not combine in such a way as to render the pharmaceutical composition unsuitable for the purpose of it's use.

A wide variety of preparation forms can be employed. Thus, if a solid carrier is used the preparation can be tableted, placed in a hard gelatin capsule in powder or pellet form or in the form of a troche or lozenge. The preparation can be in the form of a syrup, emulsion or soft gelatin capsule, it can be a sterile injectable liquid such as aqueous or non-aqueous liquid suspension.

The method in accordance with this invention comprises administering internally to an animal organism the lower alkyl-N-phenyl-N-methyl carbamoyl glycinate, usually combined with a pharmaceutical carrier, in an amount sufficient to produce anti-convulsant activity. The active medicament will be administered in a dosage unit. The route of administration may be orally or parenterally.

The pharmaceutical preparations are made following the conventional techniques of the pharmaceutical chemist involving mixing, granulating and compressing when necessary, or variously mixing or dissolving the ingredients as appropriate to the desired end product.

The following examples illustrate the preparation of lower alkyl-N-phenyl-N-methyl carbamoyl glycinates; the incorporation of such into pharmaceutical compositions of the invention; and the method of use. The examples are not intended to be construed as limiting the invention set forth in the claims.

EXAMPLE I

Preparation of Ethyl-N-Phenyl-N-Methyl Carbamoyl Glycinate

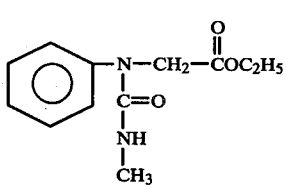

A solution of ethyl-N-phenyl glycinate (8.9 grams, 0.05 moles) and methylisocyanate (5.9 grams, 0.1 mole) was stirred in toluene (25 ml) at 35° C. for six hours. The volatiles were removed under vacuum and 60 ml of ethanol was added to the residue and evaporated. The residue was crystallized from hexane and 6.0 grams (0.25 moles) of the above-identified product was recovered having a melting point of 69° C.

EXAMPLE II

Preparation of Isobutyl-N-Phenyl-N-Methyl Carbamoyl Glycinate

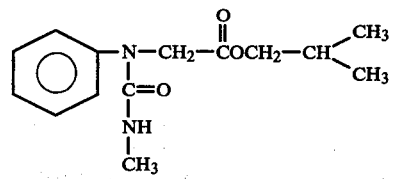

15.52 grams (0.075 mole) of isobutyl-N-phenyl glycinate was dissolved in 30 ml of chloroform. 5.7 grams (0.1 mole) of methylisocyanate was added thereto and the solution was stirred at 35° C. for six hours. The volatiles were removed under vacuum and 60 ml of ethanol was added to the residue and evaporated. The residue separated into a semi solid which was crystallized from a mixture of methyl isobutyl ketone and hexane. 6.0 grams (0.22 moles) of the above-identified product was recovered having a melting point of 57° C.

EXAMPLE III

Preparation of n-butyl-N-methylcarbamoyl glycinate

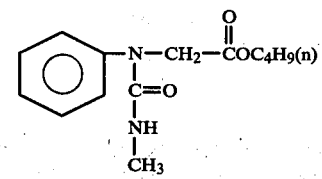

8.28 grams (0.04 moles) of n-butyl-N-phenyl glycinate was dissolved in 20 ml of toluene. 2.85 grams (0.05 moles) of methylisocyanate was added thereto and the solution was heated and maintained at 40° C. for 23 hours with intermittent agitation. The volatiles were removed under vacuum and the residue was allowed to stand overnight at room temperature. The semi-solid residue was crystallized from a mixture of carbon tetrachloride and hexane yielding 6.4 grams (0.024 moles) of the above-identified product having a melting point of about 71° C.

EXAMPLE IV

Preparation of Methyl-N-Phenyl-N-Methyl Carbamoyl Glycinate

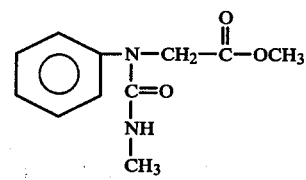

24.7 grams (0.15 moles of methyl-N-phenyl glycinate was dissolved in 30 ml of chloroform. 10.83 grams (0.19 mole) of methylisocyanate was added thereto and the solution was stirred at room temperature for 10 hours.

The volatiles were removed and ethanol (20 ml) was added and removed under vacuum. 30 ml of hexane was added to the residue and the resulting solid was recrystallized from cyclohexane to produce 6.0 grams of the above-identified product having a melting point of 74° C.

EXAMPLE V

Pharmaceutical Tablet

TABLE 1

| Ingredients | mg/Tablet |
|---|---|
| isobutyl-N—phenyl-N—methyl carbamoyl glycinate | 25 |
| Calcium sulfate dihydrate | 150 |
| Sucrose | 25 |
| Starch | 15 |
| Talc | 5 |
| Stearic Acid | 3 |

Tablets containing isobutyl-N-phenyl-N-methyl carbamoyl glycinate are prepared containing the ingredients and amounts thereof set out in Table 1. The sucrose, calcium sulfate and isobutyl-N-phenyl-N-methylcarbamoyl glycinate are thoroughly mixed and granulated with warmed 10 percent gelatin solution. The wetted mass is passed through a mesh screen directly onto drying trays. The granules are dried and passed through a smaller mesh screen, mixed with starch, talc and stearic acid and compressed into tablets.

(a) Laboratory Test Animal Preparation

Adult male, Carworth Farms #1, Laboratory mice weighing an average of 20 grams each, were intraperitoneally administered, in a volume of 0.01 ml/g body weight, a 30% aqueous polyethylene glycol 400 solution containing the active medicament in 30, 100 and 300 mg (medicament)/kg (test animal body weight) dosage levels.

(b) Maximal Electroshock Seizure Test

About 30 minutes after administration of the medicament and again about 4 hours after administration, a drop of 0.9% aqueous sodium chloride solution was instilled in each eye of the test animal, electrodes were contacted with the cornea and an alternating current of 60 Hz at 50 mA was delivered for 0.2 seconds thereto. The animal was observed for tonic extension and terminal clonus.

(c) Subcutaneous Pentylenetetrazol Threshold Test

About 30 minutes after administration of the medicament and again about 4 hours after administration, a 0.085% solution of pentylenetetrazol in 0.9% aqueous sodium chloride was administered subcutaneously to the test animal in a loose fold of skin on the back of the neck in a dose of 85 mg/kg. The animal was observed for 30 minutes for duration of clonic spasms.

(d) Rotorod Toxicity Test

About 30 minutes after administration of the medicament and again about 4 hours after administration, the laboratory animal was placed on a one inch in diameter knurled plastic rod rotating at 6 rpm. The animal was observed for at least one minute for its ability to maintain its equilibrium on the rotating rod.

Samples of ethyl-n-phenyl-N-methyl carbamoyl glycinate, n-butyl-N-phenyl-N-methyl carbamoyl glycinate, methyl-N-phenyl-N-methyl carbamoyl glycinate and isobutyl-N-phenyl-N-methyl carbamoyl glycinate, prepared by the process of examples 1-4 were tested by NINCDS as active medicaments and reported as displaying anti-convulsant activity in both tests. Ethyl-N-phenyl-N-methyl carbamoyl glycinate and isobutyl-N-phenyl-N-methyl carbamoyl glycinate, at doses of 100 mg/kg or less; in the Maximal Electroshock Seizure test the hind limb tonic extensor component was found to be repressed; and, in the subcutaneous pentylenetetrazol seizure threshold test, spasms did not last longer than 5 seconds. In addition NINCDS reported that the test animals were able to maintain their equilibrium on the rotating knurled rod in the Rotorod Ataxia test, indicating no neurological deficit. N-butyl-N-phenyl-N-methyl carbamoyl glycinate and methyl-N-phenyl-N-methyl carbamoyl glycinate were reported by NINCDS as repressing the hind limb tonic extensor component in the Maximal Electroshock Seizure test, repressing spasms in the subcutaneous pentylenetetrazol seizure threshold test, and displaying no neurological deficit in the Rotorod Ataxia test at levels above 100 mg/kg.

I claim:

1. An anti-convulsant compound of the formula:

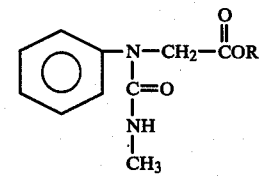

wherein R is lower alkyl.

2. A compound of claim 1 wherein R is from 1-4 carbon atoms.

3. A compound of claim 1 selected from the group consisting of ethyl-N-phenyl-N-methyl carbamoyl glycinate, n-butyl-N-phenyl-N-methyl carbamoyl glycinate and isobutyl-N-phenyl-N-methyl carbamoyl glycinate.

4. A compound of claim 1 wherein R is ethyl.
5. A compound of claim 1 wherein R is isobutyl.
6. A compound of claim 1 wherein R is methyl.
7. A compound of claim 1 wherein R is n-butyl.
8. A method of producing anti-convulsant activity which comprising administering internally, to an animal organism in need of such activity, an amount of a compound of the formula:

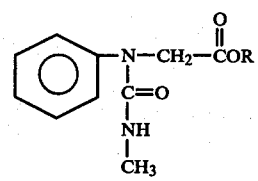

wherein R is lower alkyl; sufficient to produce said activity.

9. The method of claim 8 wherein the active ingredient is administered orally.
10. The method of claim 9 wherein the active ingredient is contained in a capsule or tablet.
11. The method of claim 8 wherein the active ingredient is administered parenterally.
12. The method of claims 8, 9, 10 or 11 wherein R is selected from methyl, ethyl, n-butyl or isobutyl.
13. A tablet or capsule pharmaceutical composition having anti-convulsant activity, in dosage unit form, comprising a non-toxic pharmaceutical carrier and an effective anti-convulsant activity inducing amount of a compound of claim 1.

* * * * *